US00RE48308E

(19) United States
(12) Reissued Patent
Fiato et al.

(10) Patent Number: US RE48,308 E
(45) Date of Reissued Patent: Nov. 17, 2020

(54) PROCESSES FOR PRODUCING FUELS AND BIOFERTILIZERS FROM BIOMASS AND PRODUCTS PRODUCED

(71) Applicants: Accelergy Corporation, Houston, TX (US); Shanghai Advanced Research Institute of the Chinese Academy of Science, Shanghai (CN)

(72) Inventors: Rocco A Fiato, Basking Ridge, NJ (US); Yuhan Sun, Shanghai (CN); Mark Allen, Littleton, CO (US); Quanyu Zhao, Shanghai (CN)

(73) Assignees: ACCELERGY CORPORATION, Houston, TX (US); SHANGHAI ADVANCED RESEARCH INSTITUTE OF THE CHINESE ACADEMY OF SCIENCE, Shanghai

(21) Appl. No.: 16/714,755

(22) Filed: Dec. 15, 2019

Related U.S. Patent Documents

Reissue of:
(64) Patent No.: 10,173,936
Issued: Jan. 8, 2019
Appl. No.: 15/149,754
Filed: May 9, 2016

U.S. Applications:
(60) Division of application No. 14/286,800, filed on May 23, 2014, now Pat. No. 9,365,461, which is a
(Continued)

(51) Int. Cl.
*C05F 11/08* (2006.01)
*C05G 3/80* (2020.01)
(Continued)

(52) U.S. Cl.
CPC ..... *C05F 11/08* (2013.01); *C05B 17/00* (2013.01); *C05D 1/00* (2013.01); *C05F 11/02* (2013.01);
(Continued)

(58) Field of Classification Search
CPC ..... A01G 31/02; A01G 31/00; C02F 1/727; C02F 1/46109; C02F 3/26; A01K 63/042;
(Continued)

(56) References Cited

U.S. PATENT DOCUMENTS 5,916,029 A * 6/1999 Smith ..... A01C 1/06 424/93.4
8,317,891 B1 * 11/2012 Cheiky ..... C05F 11/02 423/445 R (Continued)

FOREIGN PATENT DOCUMENTS

WO 2008/079029 A2 * 7/2008

*Primary Examiner* — Jerry D Johnson

(57) ABSTRACT

An IBTL system having a low GHG footprint for converting biomass to liquid fuels in which a biomass feed is converted to liquids by direct liquefaction and the liquids are upgraded to produce premium fuels. Biomass residues from the direct liquefaction, and optionally additional biomass is pyrolyzed using microwave pyrolysis to produce structured biochar, hydrogen for the liquefaction and upgrading, and $CO_2$ for conversion to algae, including blue green algae (cyanobacteria) in a photobioreactor (PBR). Produced algae and diazotrophic microorganisms are used to produce a biofertilizer that also contains structured biochar. The structured biochar acts as a nucleation agent for the algae in the PBR, as a absorption agent to absorb inorganics from the biomass feed to direct liquefaction or from the liquids produced thereby, and as a water retention agent in the biofertilizer. The ratio of cyanobacteria to diazotrophic microorganisms in the biofertilizer can be selected so as to achieve desired total chemically active carbon and nitrogen contents in the soil for a given crop.

19 Claims, 2 Drawing Sheets

Related U.S. Application Data continuation of application No. 61/855,789, filed on May 23, 2013.

(51) Int. Cl.

| | |
|---|---|
| ***C05B 17/00*** | (2006.01) |
| ***C05D 1/00*** | (2006.01) |
| ***C05F 11/02*** | (2006.01) |
| ***C10B 19/00*** | (2006.01) |
| ***C10B 53/02*** | (2006.01) |
| ***C10G 1/00*** | (2006.01) |
| ***C10G 1/06*** | (2006.01) |
| ***C10G 1/08*** | (2006.01) |
| ***C12N 1/12*** | (2006.01) |
| ***C12N 1/20*** | (2006.01) |

(52) U.S. Cl.

CPC ..... *C05G 3/80* (2020.02); *C10B 19/00* (2013.01); *C10B 53/02* (2013.01); *C10G 1/002* (2013.01); *C10G 1/06* (2013.01); *C10G 1/065* (2013.01); *C10G 1/083* (2013.01); *C10G 1/086* (2013.01); *C12N 1/12* (2013.01); *C12N 1/20* (2013.01); *C10G 2300/1011* (2013.01); *C10G 2400/02* (2013.01); *C10G 2400/04* (2013.01); *C10G 2400/08* (2013.01); *Y02E 50/14* (2013.01); *Y02E 50/32* (2013.01); *Y02E 50/343* (2013.01); *Y02P 20/125* (2015.11); *Y02P 20/134* (2015.11); *Y02P 20/145* (2015.11); *Y02P 30/20* (2015.11); *Y02T 50/678* (2013.01); *Y02W 30/47* (2015.05)

(58) Field of Classification Search

CPC .... Y02P 60/216; Y02P 20/134; Y02P 20/125; Y02P 20/145; Y02P 30/20; C05F 11/08; C05F 11/02; C05G 3/80; C10B 19/00; C10B 53/02; C12N 1/20; C12N 1/12; C10G 1/002; C10G 1/065; C10G 1/083; C10G 1/086; C10G 1/06; C10G 2300/1011; C10G 2400/02; C10G 2400/04; C10G 2400/08; C05B 17/00; C05D 1/00; Y02E 50/14; Y02E 50/32; Y02E 50/343; Y02T 50/678; Y02W 30/47

See application file for complete search history.

(56) References Cited

U.S. PATENT DOCUMENTS

| | | | | |
|---|---|---|---|---|
| 8,361,186 | B1 * | 1/2013 | Shearer | C05F 5/00 71/32 |
| 8,568,493 | B2 * | 10/2013 | Cheiky | C01B 32/05 44/628 |
| 9,725,371 | B2 * | 8/2017 | Shearer | C05F 11/02 |
| 2002/0064495 | A1 | 5/2002 | Miura | |
| 2011/0172092 | A1 | 7/2011 | Lee | |
| 2012/0029252 | A1 | 2/2012 | Lissianski | |
| 2012/0144887 | A1 * | 6/2012 | Fiato | C05F 17/40 71/7 |
| 2012/0208254 | A1 | 8/2012 | Smith | |
| 2015/0128672 | A1 * | 5/2015 | Shearer | C05D 9/02 71/24 |
| 2017/0327428 | A1 * | 11/2017 | Shearer | C05F 11/00 |

* cited by examiner

PROCESSES FOR PRODUCING FUELS AND BIOFERTILIZERS FROM BIOMASS AND PRODUCTS PRODUCED

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates to integrated biomass to liquids processes in which $CO_2$ and inorganic emissions are substantially reduced or eliminated by using $CO_2$ to produce algae and the use of the blue green algae plus diazotrophic microorganisms together with other liquefaction byproducts for producing specifically formulated biofertilizers. This invention also relates to more effective biofertilizer formulations than are possible with the prior art and to methods of simultaneously controllably increasing the chemically active carbon and nitrogen content of the soils.

BACKGROUND OF THE INVENTION

Increases in the cost of petroleum and concerns about future shortages has led to increased interest in other carbonaceous energy resources, such as biomass for the production of useful fuel and chemical products. Biomass is an important component of a comprehensive energy strategy for use of domestic resources to insure energy independence and to simultaneously reduce the overall GHG footprint of associated processes. Various processes have been proposed for converting such materials to liquid and gaseous fuel products including gasoline, diesel fuel, aviation fuel and heating oils, and, in some cases, to other products such as lubricants, chemicals and synthetic fertilizers.

A number of problems that have hampered widespread use of these routes include the relatively low thermal efficiency of conventional technologies and the inability to use various process by-products such as $CO_2$, char and waste inorganics for beneficial effects. The conversion of all or selected portions of the biomass, which has a hydrogen to carbon (H/C) ratio of approximately 1:1 up to about 2:1, to hydrocarbon products, such as fuels that have H/C ratio of something greater than 2:1, results in up to half of the carbon in the biomass being converted to $CO_2$ and vented to the atmosphere, and thereby wasted. Additionally, the fact that, heretofore, a large amount of greenhouse gas (GHG), particularly in the form of $CO_2$, is emitted to the atmosphere as a waste product in the conversion of biomass to useful products has caused biomass to liquids (BTL) processes to be questioned by many from an environmental point of view.

It has been proposed to at least partially overcome the GHG problem by capturing and sequestering the carbon dioxide by re-injecting it into subterranean formations. Such an arrangement has the disadvantages of being expensive, of further reducing the process energy efficiency, of requiring the availability of appropriate subterranean formations somewhere in the vicinity of the conversion facility, of concerns about the subsequent escape into the atmosphere of the carbon dioxide, and the waste of the energy potential of the carbon content of the carbon dioxide.

Direct pyrolysis methods have been developed for liquefying carbonaceous materials such as biomass, but these too generate unwanted byproducts such as char and inorganics that are of limited or no value. Moreover, none of these proposed arrangements achieve the combination of thermal efficiency, low cost and substantially reduced GHG emissions that would be required for them to be economically and environmentally attractive. There remains an important need for economical biomass to liquids conversion processes with reduced carbon dioxide emissions coupled with the efficient use of the $CO_2$, carbon and inorganic byproducts.

SUMMARY OF THE INVENTION

In accordance with one aspect of the invention there has been developed a highly efficient integrated biomass to liquids (IBTL) process scheme for producing both liquids, such as premium fuels and chemical feedstocks, and novel, self-replicating biofertilizers that substantially reduce, or even eliminate, the carbon footprint of the integrated process. The integrated process involves four major steps:

1—directly liquefying all or part of the biomass feed by hydroprocessing;

2—producing structured biochar and hydrogen by pyrolyzing biomass residues from the liquefaction step and, optionally, a portion of the biomass feed;

3—upgrading the liquids to produce fuels and/or chemical feedstocks; and

4—using process produced $CO_2$ to produce algae based biofertilizers.

In accordance with an important aspect of the invention, the structured biochar produced during the pyrolysis is used as a nucleation agent for facilitating the production of the algae, as absorption agent for extracting inorganics, such as phosphorus, potassium and other metals, from the biomass feedstock prior to liquefaction or from the liquid product of the liquefaction, and/or as a carrier component of the biofertilizer of the invention. In accordance with another aspect of the invention, the pyrolysis conditions are controlled to produce biochar having controlled pore sizes that substantially optimize its utility either as an algae nucleation agent, absorption agent, or as a water retention agent in the produced biofertilizer. The incorporation in the biofertilizer of biochar that has been used as an absorption agent has the significant benefit of adding beneficial mineral constituents such as phosphorus and potassium to the biofertilizer. Additional beneficial constituents from other sources can also be absorbed into biochar used as part of the biofertilizer. The use of the biochar as an absorption agent has a further advantage that the pore size of the biochar can be controlled such that the water or other beneficial constituents are released into the soil at a roughly controlled rate, thereby providing a "timed release" function.

The biomass feedstock may be obtained from seed crops, byproducts in food crop production, waste products from fanning, food production, cooking oil, municipal operations, or other conventional sources, and/or algae. All or part of the hydrogen required for the hydroprocessing and/or upgrading steps can be supplied by the hydrogen produced during pyrolysis or, alternatively, from another source.

The conversion of process produced $CO_2$ to algae and especially to blue green algae (cyanobacteria), is preferably performed in a closed photobioreactor (PBR), although an open PBR can also be used. Some of the produced algae may be used as part of the biomass. Preferably, all or most of the algae is used to produce the biofertilizer of the invention.

Preferably, the bio fertilizer of the invention also includes nitrogen fixing and/or phosphate solubilizing diazotrophic organisms such as Rhizobium, Azotobacter and Azospirillum that are preferably produced separately from the algae producing PBR. The concentration and composition of such diazotrophic organisms in the biofertilizer made be selected based on the composition of the soil to which the biofertilizer is to be applied and the particular crops which are to be grown therein to provide the desired amount of nitrogen fixation for the particular application.

After inoculation of soil with an algae-based biofertilizer, especially blue green algae (cyanobacteria), the algal and diazotrophic microorganisms repopulate the soil through natural reproduction, using sunlight, nitrogen and $CO_2$ from the atmosphere, at much higher concentration than originally applied to the soil, thereby substantially reducing, or even eliminating, the CO2 footprint of the overall IBTL process on a lifecycle basis and substantially increasing the fertility of the soil for plant growth.

The biofertilizer of the invention preferably includes a soil inoculant cultured from the set of microorganisms including cyanobacteria that are already present, or are similar to those already present. in the soil or type of soil to which the biofertilizer is to be applied. The biofertilizer soil application rates can range from one gram per square meter to greater than 25 grams per square meter depending on soil type and soil moisture. This provides a highly leveraged effect on soil (terrestrial) carbon sequestration and greatly increases the fertility of the soil. Starting with one ton of $CO_2$ produced in the BTL process, the use of the biofertilizer of the invention can result, on a lifecycle basis, in several tens of tons of additional $CO_2$ being removed from the atmosphere and sequestered in the treated soil. In accordance with a still further aspect of the invention, during times such as cloudy days or at night when there is not enough available ambient sunlight to drive the photosynthesis for producing algae, CO2 produced by the IBTL process of the invention may be stored until sunlight is available, e.g., by liquefying the CO2 or by storing it under pressure in bladders that can be part of or adjacent to the PBRs being used to produce the blue green algae. Alternatively, it is also possible to illuminate the contents of the PBR during non-sunlit hours in order to maintain the productivity of the algae.

Important advantageous synergies in the IBTL process and system of the present invention that contributed substantially to its overall efficiency and economic attractiveness include the facts that the CO2 stream produced during pyrolysis and liquefaction is highly concentrated and an ideal feed for producing algae, and that the $NH_3$ inherently produced in the upgrading step is an important nutrient in the algae production step. When a finely divided molybdenum catalyst is used in the liquefaction step, the molybdenum catalyst can be prepared in situ from a phosphomolybdic acid (PMA) precursor. Advantageously, phosphorus can be isolated from the PMA catalyst precursor, and used as a nutrient in algae production. Also oxygen produced in the production of algae can be supplied to the pyrolysis system.

In addition to the advantages of the integrated biomass to liquids process of the invention in maximizing the use of process produced $CO_2$ to make algae-based biofertilizers that beneficially incorporate multiple, otherwise substantially worthless, reaction byproducts, such as char and inorganics, the self-replicating nature of such formulated biofertilizers terrestrially sequester very large additional amounts of atmospheric $CO_2$ that greatly magnifies the overall carbon sequestration potential of the process or the invention.

DETAILED DESCRIPTION OF EMBODIMENTS

Figure 1:
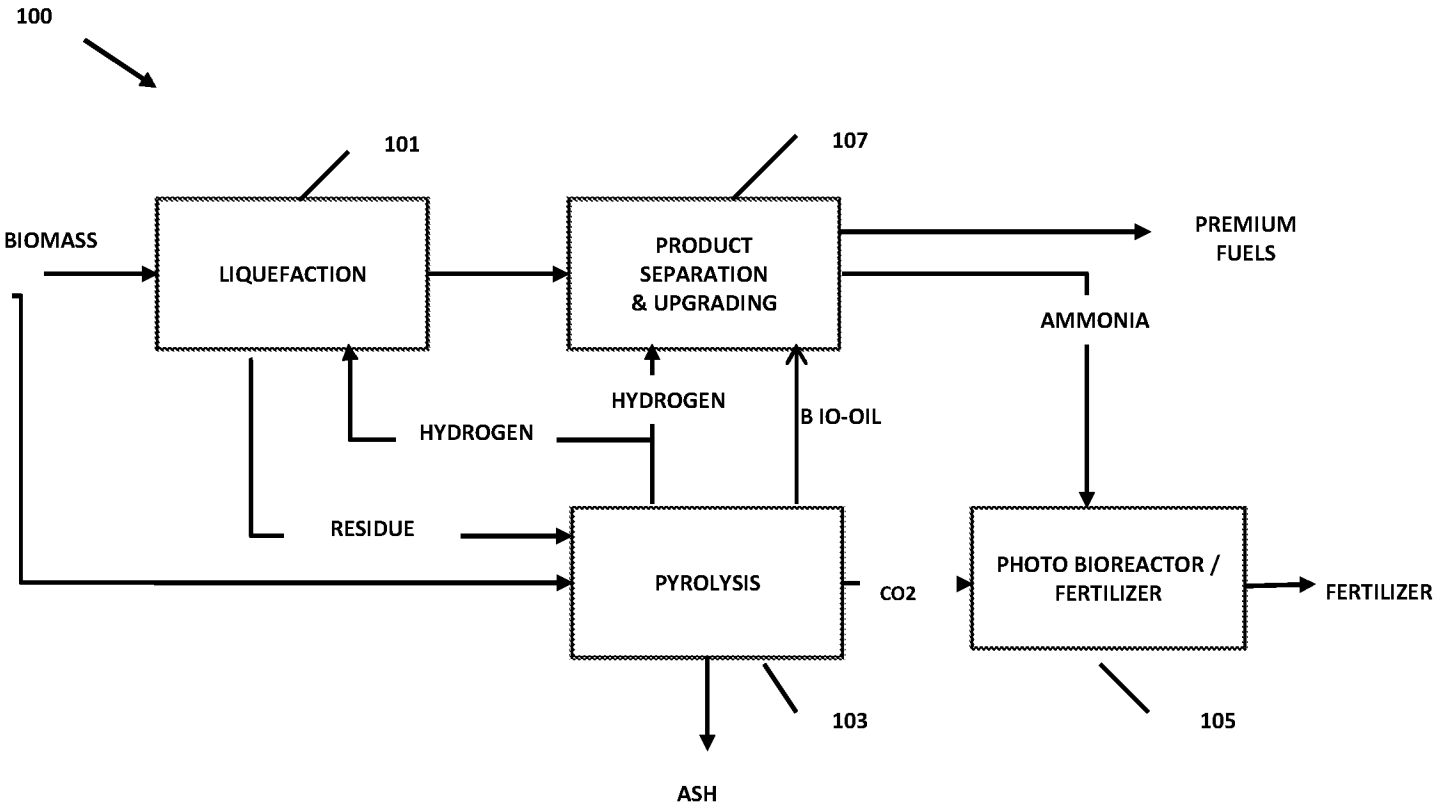
FIG. 1 is a simplified flow chart of one embodiment of an integrated biomass-to-liquids system with production of fertilizer from algae in accordance with the invention.

Referring now to FIG. 1 of the drawings, there is illustrated a preferred embodiment of the integrated biomass to liquids (IBTL) process and system of the invention, in which biomass is converted to liquids in the liquefaction system 101 and biomass residues from the liquefaction step and/or other carbon containing process wastes and, optionally additional biomass, are pyrolyzed in the pyrolysis system 103 to produce structured biochar, hydrogen, bio oil and, optionally, syngas for an indirect liquefaction process such as Fischer Tropsch synthesis or methanol synthesis (not shown). The biomass feedstock may be obtained from seed crops, byproducts in food crop production, waste products from farming, food production, cooking oil, municipal operations, or other conventional sources, and/or algae. The pyrolysis system 103, when operated with water or oxygen co-feed, or the hydrogen production systems of the integrated IBTL process also generates large amounts of concentrated, pure CO2 which is supplied to the algae production system 105 that preferably includes one or more closed photobioreactors (PBR's) to produce algae through photosynthesis, and particularly cyanobacteria (blue green algae).

The biomass feed to the liquefaction system 101 may either be (a) raw biomass, preferably from which most of the H2O has been removed, (b) triglycerides that have been extracted from the raw biomass with the biomass residue after triglyceride extraction being fed to the pyrolysis system 103, or (c) fatty acid methyl esters that have been produced by trans-esterifying the triglycerides. The specific nature of the feed will determine the overall stoichiometric volume of hydrogen required to achieve desired hydrocarbon production in the liquefaction step.

Removing unwanted components of the biomass feed before liquefaction by first extracting the lipids and further by converting the lipids to fatty acid methyl esters has the advantages of allowing the use of less $H_2$ during the liquefaction process and the ability to achieve better control of product selectivity. Preferably the inorganics, such as potassium phosphorus and other metals, in the biomass feed are also removed either from the feed prior to liquefaction or from the liquid product by absorption by a bed of biochar such as produced by the pyrolysis system 103.

The produced blue green algae is a primary component of the biofertilizer composition of the invention. Preferably, nitrogen fixing diazotrophic organisms are also constituents of the biofertilizer composition. A portion of the produced algae may optionally be used as an additional feed to the liquefaction system 101 and/or the pyrolysis system 103.

Structured biochar produced in the pyrolysis system 103 is used to provide nucleation sites for the production of algae in the PBR system 105, as an absorbent agent to remove phosphorus, potassium and other metals from the biomass feed or produced liquids in the liquefaction system 101, and as a component of the biofertilizer of the invention in which the absorbed inorganics and other absorbed materials in the biochar act as nutrients to impart beneficial properties to the biofertilizer. By structured biochar is meant biochar that has been produced by a method, such as microwave pyrolysis, that enables a substantial degree of control of its macro and micro pore structure, such that the pore structure produced in the biochar has a roughly controlled pore diameter and length.

The liquids produced in the liquefaction system 101 and the bio oil from the pyrolysis system 103 are fed to the product separation and upgrading system 107 in which they are upgraded to produce premium fuels such as gasoline, diesel and jet fuel, and/or chemical feedstocks. The upgrading system 107 also produces $NH_3$, which is fed to the algae production system 105 as a nutrient. Phosphorus can also be recovered from the PMA catalyst precursor if the liquefaction system incorporates the use of a molybdenum catalyst. Optionally, as an alternative, an additional natural gas feed may be reacted by steam methane reforming (SMR), to produce additional hydrogen for the liquefaction and upgrading steps, and syngas for indirect liquefaction.

Catalysts useful in the liquefaction process also include those disclosed in U.S. Pat. Nos. 4,077,867, 4,196,072 and 4,561,964, the disclosures of which are hereby incorporated by reference in their entirety. Pyrolysis processes and reactor systems suitable for use in the system of the invention are disclosed in U.S. Published Patent Patent Application Nos. US2012/0237994 and US2008/02647771, the disclosures of which are hereby incorporated by reference in their entirety.

Figure 2:
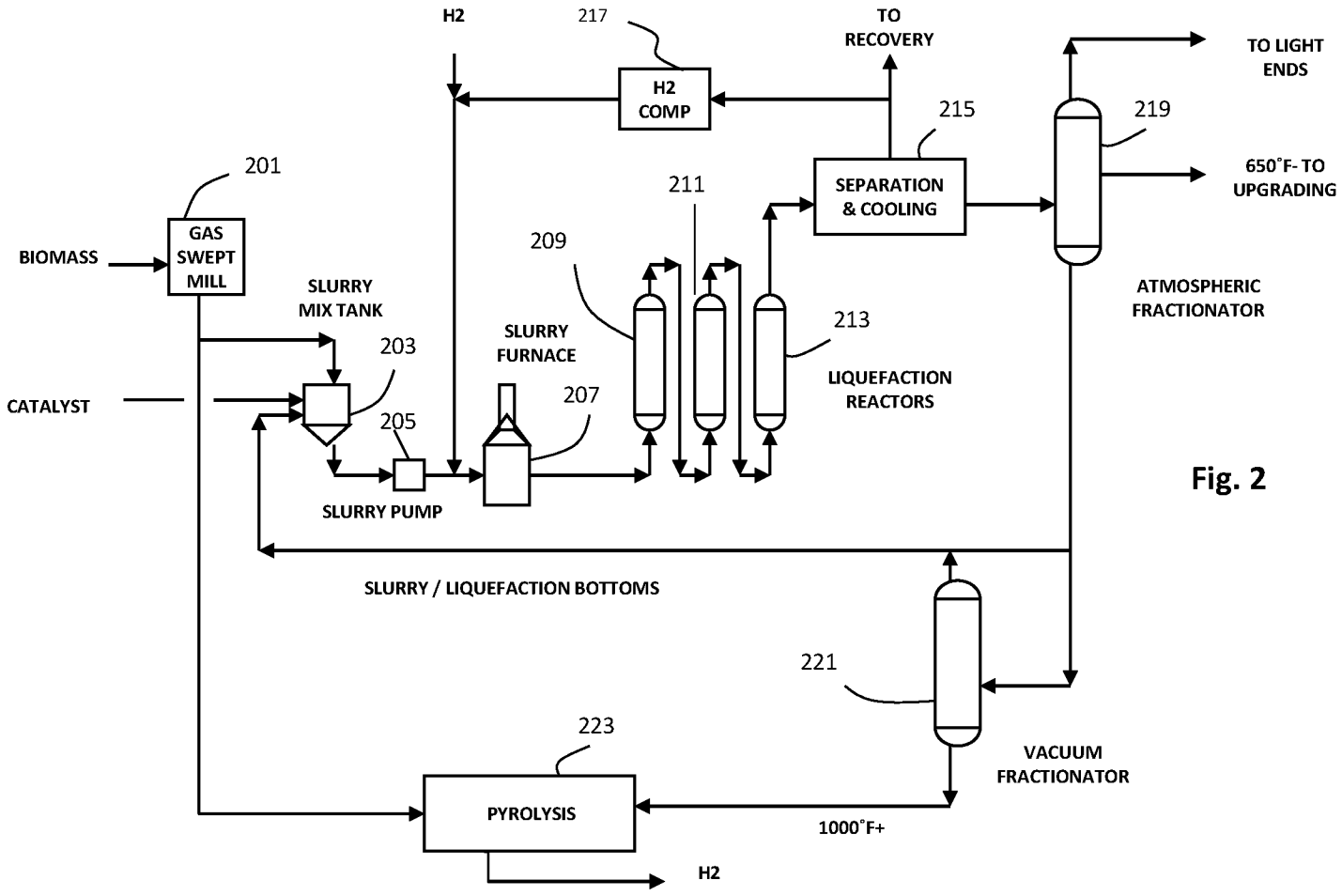
FIG. 2 is a schematic diagram of a biomass conversion system suitable for use in the illustrated embodiments of the invention.

An illustrative embodiment of a reactor system suitable for performing the liquefaction of biomass in accordance with the invention is shown in FIG. 2 of the drawings. The biomass feed is dried and crushed in a conventional gas swept roller mill 201 to a moisture content of 1 to 4%. The crushed and dried biomass is fed into a mixing tank 203 where it is optionally mixed with a carrier solvent containing recycled bottoms and optionally a liquefaction catalyst precursor to form a slurry stream.

Typical operating temperature ranges from 250 to 600° F. and more preferably between 300 and 450° F. From the slurry mix tank the slurry is delivered to the slurry pump 205. The selection of the appropriate mixing conditions is based on experimental work quantifying the rheological properties of the specific slurry blend being processed.

The slurry leaves the mixing tank 203 at about 300 to 500° F. (139 to 260° C.). Most of the moisture in the biomass is driven off in the mixing tank due to the hot recycle solvent (650/1000° F. or 353/538° C.) and bottom feeding to the mixing tanks. Such moisture and entrained any volatiles are condensed out as sour water (not shown in FIG. 2). The biomass in the slurry leaving the mixing tank 203 has about 0.1 to 1.0% moisture. The biomass slurry is pumped from the mixing tank 203 and the pressure raised to the desired level by the slurry pumping system 205. The resulting high pressure slurry is preheated in a heat exchanger (not shown), optionally mixed with hydrogen, and then further heated in furnace 207.

The biomass slurry (and optional hydrogen mixture) is fed to the input of the first stage of the series-connected liquefaction reactors 209, 211 and 213 at about 600 to 700° F. (343° C.) and 2,000 to 3,000 psig (138 to 206 kg/cm$^2$ g). The reactors 209, 211 and 213 are up-flow tubular vessels, the total length of the three reactors being 50 to 150 feet. The temperature rises from one reactor stage to the next as a result of various exothermic reactions. In order to maintain the maximum temperature in each stage below about 850 to 900° F. (454 to 482° C.), additional hydrogen is preferably injected between reactor stages. The hydrogen partial pressure in each stage is preferably maintained at a minimum of about 1,000 to 2,000 psig (69 to 138 kg/cm$^2$ g). The effluent from the last stage of liquefaction reactor is separated into a gas stream and a liquid/solid stream, and the liquid/solid stream let down in pressure, in the separation and cooling system 215. The gas stream is cooled to condense out the liquid vapors of naphtha, distillate, and solvent. The remaining gas is then processed to remove $H_2S$ and $CO_2$.

Most of the processed gas is then sent to the hydrogen recovery system 217 for further processing by conventional means to recover the hydrogen, contained therein, which is then recycled to be mixed with the biomass slurry. The remaining portion of the processed gas is purged to prevent buildup of light ends in the recycle loop. Hydrogen recovered therefrom is used in the downstream hydro-processing upgrading system.

The depressurized liquid/solid stream and the hydrocarbons condensed during the gas cooling are sent to the atmospheric fractionator 219 where they are separated into light ends, naptha, distillate and bottoms fractions. The light ends are processed to recover hydrogen and $C_1$-$C_4$ hydrocarbons that can be used for fuel gas and other purposes. The naphtha is hydrotreated to saturate diolefins and other reactive hydrocarbon compounds. The 160° F.+ fraction of the naptha can be hydrotreated and power formed to produce gasoline. The distillate fraction can be hydrotreated to produce products such as diesel and jet fuel.

The atmospheric fractionator 219 is preferably operated at a high enough pressure so that a portion of the 600 to 700° F.+ (315 to 371° C.+) bottoms fraction can be recycled to the slurry mixing tank 203 without pumping for use as the solvent.

The remaining bottoms produced from the atmospheric fractionator 219 are fed to the vacuum fractionator 221 wherein it is separated into of 1000° F.− fraction and a 1000° F.+ fraction. The 1000° F.− fraction is added to the solvent stream being recycled to the slurry mix tank 203.

The 1000° F.+ fraction is fed to the bottoms pyrolysis system 223 where it is heated in a closed to reactor vessel under a controlled atmosphere to a temperature of between 320 and 750° C. for period of 5 minutes to 3 or more hours to convert the reactor contents to biochar, bio-oil, H2, CO2 and CO. The pyrolysis atmosphere can contain controlled concentrations of oxygen and steam. If the atmosphere contains essentially no steam or oxygen, the production of bio-liquid and biochar is maximized. As the amount of steam and O2 is increased, the pyrolysis system 223 produces increasing amounts of H2, CO2 and CO and less bio-liquid and biochar. If additional hydrogen is needed for the biomass liquefaction and upgrading of the products thereof, a portion of the biomass from the gas swept roller mill 201 is fed to the pyrolysis system 223 for producing the additional required hydrogen. The biochar produced in the pyrolysis system 223 can be can be used as a algae nucleating agent in the photobioreactors 105, as an absorption agent for removing metals from the biomass prior to liquefaction, and as component in the ultimate biofertilizer.

A process for upgrading the liquid products of the liquefaction system 101 and the pyrolysis system 103 is disclosed in U.S. Pat. No. 5,198,099, the disclosure of which is hereby incorporated by reference in its entirety. Other processes and systems suitable for upgrading the liquid products of the liquefaction system 101 and the pyrolysis system 103 are commercially available from vendors such as Haldor Topsoe, UOP, Axens, Criterion and others.

The gas from the pyrolysis system 223, which contains $H_2S$, CO2, and $H_2$ is then sent to a separation system such as Rectisol or Selexol. One key advantage of Selexol is that it produces the CO2 at higher pressure than scrubbing processes such as MEA. This reduces the amount of compression required to store the CO2 or to transport the CO2 to the algae production system 111. The $H_2S$ and COS, once hydrolyzed, are removed by dissolution in, or reaction with, an organic solvent and converted to valuable by-products such as elemental sulfur or sulfuric acid. UOP and others license the Selexol Process.

Fischer Tropsch (FT) Synthesis

Reactors, catalysts and conditions for performing FT synthesis are well known to those of skill in the art and are described in numerous patents and other publications, for example, in U.S. Pat. Nos.7,198,845, 6,942,839, 6,315,891, 5,981608 and RE39,073, the contents of which are hereby incorporated by reference in their entirety. FT synthesis can be performed in fixed bed, moving bed, fluid bed, ebulating bed or slurry reactors using various catalysts and under various operating conditions that are selected based on the desired product suite and other factors. Typical FT synthesis products include paraffins and olefins, generally represented by the formula $nCH_2$. The productivity and selectivity for a given product stream is determined by reaction conditions including, but not limited to, reactor type, temperature, pressure, space rate, catalyst type and syngas composition.

The stoichiometric syngas $H_2/CO$ ratio for FT synthesis is about 2.0. The ratio of $H_2/CO$ in syngas produced from biomass is less than 2, and typically from about 0.5 up to 1.0. This ratio can be increased by mixing the biomass produced syngas with syngas produced from light hydrocarbons or natural gas. If such mixing step does not increase the $H_2/CO$ ratio adequately, and additional hydrogen is not conveniently available from other sources, such ratio may be farther increased by the water-gas shift reaction. In the case of FT synthesis conversion performed using a cobalt-based catalyst, which does not promote a water-gas shift reaction, the $H_2/CO$ ratio of biomass produced syngas is preferably increased to about 2.0 before being introduced in the FT synthesis reactor, e.g., by hydrogen produced by the syngas generating system 109. If the FT synthesis conversion is being performed using an iron-based catalyst, which does provoke the water-gas shift reaction, it is not necessary to use a separate shift converter. In any case, however, the water-gas shift reaction generates additional $CO_2$.

Hydrodeoxygenation

If the feed to the liquefaction system 101 consists entirely of biomass, such as lipids extracted from algae and/or other biomass sources. the liquefaction system 101 can alternatively be implemented using a catalytic hydrodeoxygenation and isomerization (CHI) system, or similar systems, such as disclosed in published international applications WO 2009/025663, WO 2009/025635, WO 2008/8124607 or U.S. Pat. No. 4,992,605, the contents of which are hereby incorporated by reference in their entireties.

CO2 Capture and Re-Use

As described above, CO2 produced by the process of the invention is captured and used to produce algae in a PBR. The PBR system can involve closed or open reactor systems; with closed systems being preferred to enable maximum production of specifically selected strain(s) of algae and to minimize water loss and the contamination of the algae strain from external sources, and to allow the capture of oxygen produced in the algae generation step for use in other combustion or pyrolysis related steps in the overall IBTL process. There are a number of commercially available algae production systems. Illustrative closed PBR systems are described in published US patent application numbers 2007/0048848, 2007/0048859, 2012/0107921, 2013/0273630 and 2008/0160591 which are incorporated herein by reference in their entirety. Preferably, structured biochar is added to the aqueous brine in the PBR to act as nucleating sites for the algae being produced and for absorbing nutrients from the brine to be included in the biofertilizer product. It has been found that the biochar in the PBR promotes "attached growth" of the algae which causes the algae to reproduce better in the PBR and makes it easier to separate the algae from the brine in later processing. The absorbed nutrients in the structured biochar also assist in the reproduction of the algae and diazotrophic organisms in the biofertilizer after it has been applied to the soil.

The algae produced in the PBR can be isolated in aqueous streams for use as a soil treatment material in order to increase the carbon content of the soil and for inducing photosynthesis to generate additional algae in the soil. Diazotrophic organisms are preferably added to the algae either before or after the algae is dried. The resulting organisms are then preferably combined with additives such as organic binders, alkali containing residues from the pyrolysis system 103 and/or liquefaction system 101, and the final mixture is used as a natural biofertilizer. In this capacity, the material not only results in further growth of algae and diazotrophic organisms in the soil via photosynthesis and thereby increasing its natural carbon content, but also causes various forms of algae, especially blue green algae (cyanobacteria), and other diazotrophic organisms to fix nitrogen, all of which promotes the growth of plant life in the treated soil and greatly reduces the GHG, and particularly the CO2, footprint of the IBTL process of the invention. The diazotrophic organisms are preferably produced separately from the algae amplifying PBR in unknown type of bioreactor such as an autoclave. In this process, the naturally occurring complement of microorganisms, including cyanobacteria, occurring in the soil or type of soil to which the biofertilizer is to be applied, or a similar suite of microorganisms, is optimized and amplified, and the resulting material is dewatered and dried and treated with desirable additives; after which it is granulated, optionally coated with materials to optimize its spreading characteristics and distributed on the soil that is to be fertilized or restored.

In addition to the beneficial reduction of the GHG footprint of the IBTL system of the invention by terrestrially sequestering the $CO_2$ consumed by algae in the production fertilizer, the integrated system of the invention has the additional extremely important advantageous characteristic that the algae and other photosynthetic microorganisms applied to the soil, especially in the case of the biofertilizer made according to the invention, because it was specifically selected to be compatible with the makeup of the soil to which it is applied and multiplies through photosynthesis, thereby extracting more $CO_2$ from the atmosphere and fixing atmospheric nitrogen. This characteristic results in an increase in the net CO2 sequestered by a factor of 30 or more, and potentially as much 150 fold over the CO2 consumed during the production of algae in the IBTL process of the invention, and greatly enriches the fertility of soil.

The quality of the natural bio-fertilizer (as affected by the quality of the water and the purity of the $CO_2$ and other nutrient streams provided to the PBR from other steps in the IBTL process of the invention) can be controlled to generate food grade/FDA certified material for use in enhancing growth of various food crops; to an intermediate grade to serve as a soil amendment material for reclamation of arid soils to prevent or inhibit wind erosion via formation of a bio-active crust; or to lower purity material for use in reclamation of spent mine soils where the addition of a bio-reactive material inhibits leaching and erosion of contaminated soils to improve the quality of water drain off. The added biochar components (described below) can be applied to further control the overall hydrophylicity and hydrophobicity of the biofertilzer formulation to further control the water retention properties of the soil. By this mechanism, it is possible to tailor the biofertilizer formulations for optimal use in the production of specific crops.

The natural biofertilizer can be used as a direct replacement for conventional ammonia based fertilizer, where it offsets the further large amounts of $CO_2$ that would otherwise be generated in production of $NH_3$ and the full range of ammonia based fertilizers. This also leads to other downstream benefits, such as a reduction in run off of $NH_3$ based components that contaminate downstream waterways and cause unwanted blooms of algae and other aquatic plants.

BioFertilizer Formulations

This invention also provides specific biofertilizer formulations comprised of different blends of the process streams from the IBTL flow scheme, the cyanobacteria and, preferably, other diazotrophic organisms, the biochar, and the inorganic residues from the pyrolysis process. It allows the elemental composition, the total nitrogen level, the total average surface area of the composition, the surface area of individual biochar components or mixtures thereof, the total alkali and composition of individual alkali components to be controlled in a way that is tailored to specific crops or end uses.

In the production of a preferred biofertilizer, a PBR is inoculated with a biological culture that can be drawn from its normal residence in the top centimeter of healthy undisturbed soil having similar soil and environmental characteristics as the soil to which the biofertilizer is to be applied, or with a biological culture that includes one or more cyanobacteria strains and preferably other photosynthetic microorganisms suitable for use as a fertilizer in the location where the biofertilizer is to be used. In nature, these soil microorganisms form a biological soil crust ("BSC") that serves many functions, including gluing the soil grains in place, thereby limiting wind and water erosion, as well as providing fertilization and plant vitality. Cyanobacteria and "cyanolichens" are a primary source of fixed atmospheric nitrogen in arid ecosystems.

Studies in the western United States have observed that between 5 to 49 cyanobacterial taxa, depending on the study site. Nostoc, Schizothrix, Anabaena, and Tolypothrix are the most frequently encountered heterocystous genera. Microcoleus and Phormidium are commonly encountered non-heterocystous genera. In western Colorado, for example, Scytonema, a heterocystous genus, is frequently observed. Heterocysts are differentiated specialized cells responsible for nitrogen fixation. Heterocysts lack the water-splitting O2-evolving Photosystem II apparatus. This adaptation has evolved to eliminate the inhibition of nitrogenase activity by O2, but still generates ATP energy by retaining photosystem-I activity.

Many non-heterocystous cyanobacterial genera are known to contain nitrogenase and may fix nitrogen in the dark under microaerophillic or anaerobic conditions. Microcoleus vaginatus is an extremely important microbiotic crust component based on its frequency of occurrence and morphology. The mucilaginous encased filaments of Microcoleus vaginatus are highly effective in binding sand particles, thus reducing erosion and producing a stable substrate for the colonization of cyanolichens and other microorganisms. Although Microcoleus vaginatus may not fix nitrogen directly, it is thought that its mucilaginous sheath provides an anaerobic micro-environment and carbon source for epiphytic diazotrophic bacteria.

Cyanolichens are also a major contributor of fixed-nitrogen and microbiotic crust ground cover in desert ecosystems. Lichens are a mutualistic symbiosis between a fungus (mycobiont) and an alga (phycobiont). In most cases, the lichen phycobiont is a green alga, usually Trebouxia, but the cyanolichen phycobiont consists of cyanobacteria, most commonly Nostoc, Scytonema, or Anabaena. These cyanolichens are characteristically black, gelatinous in texture, and non-stratified. Certain stratified lichens inhabiting subalpine biomes, such as Peltigera and Lobaria, contain both the green Trebouxia, and the nitrogen-fixing cyanobacterium, Nostoc. For example, the cyanolichens of the arid western United States can occupy from 40 to 100% of the ground cover and make significant contributions towards soil stabilization and N.sub.2-fixation. Depending on the soil and abiotic environment, up to 159 lichen species representing 53 genera have been observed. Some of the most commonly encountered genera include, Collema, Placinthium, Leptogium, and Heppia.

The cyanobacterial genera to be exploited may be obtained from biological soil crusts and include, but are not limited to the following genera: Nostoc, Anabaena, Scytonema, Tolypothrix, Calothrix, Microcoleus, Rivularia, Phormidium, Symploca, Schizothrix, Stigonema, Plectonema, and Chroococcus. In addition to these cyanobacteria, it can be desirable to include eukaryotic algae such as Chlamydomonas, Trebouxia, Scenedesmus, for instance. It is also desirable to include free-living nitrogen-fixing bacteria, such as Azotobacter, Rhodospirillium, or Rhodopseudomonas, for example. Other important soil bacteria such Arthrobacter and various actinomycetes including the genera, Frankia, Nocardia, Streptomyces, and Micromonospora may be included to enhance nutrient cycling. Finally, it may also be desirable to include lichenizing, saprophytic, and mycorrhizal fungi to complete the microbial complement of the basic photosynthetic biofertilizer. These heterotrophic microorganisms will be produced using standard methods.

The biofertilizer is preferably designed, in addition to providing soil nitrogen and carbon, to behave as an erosion control agent. In most cases, the biofertilizer alone will achieve the desired results. Based on the flexibility of the biofertilizer, it can be used in conjunction with traditional erosion control methods such as fibrous mulches and tackifiers thus enhancing the efficacy of these traditional products. For instance, hard-rock mine tailings, waste and overburden characteristically become acidic (pH<3) through the oxidation of sulfur by bacteria. These acidic environments inhibit seed germination, and exceeds the lower pH limit of cyanobacteria (pH<5). However, it has been shown that when a layer of mulch is applied to the surface, it serves as a chemical insulator that permits seed germination and the growth of the biofertilizer. The plant roots penetrate into the nitrogen-deficient acidic mine tailings and continue to grow when nitrogen is supplied by the biofertilizer.

It has it has been found that rhizobacteria are a key component of the microorganisms found in soils. It is believed that cyanobacteria, particularly when present in combination with rhizobacteria, act as a phyto stimulator and generate organic acids including gibberellic acid and acetic acid and other mono and poly carboxylic acids, that help dissolved minerals in the soil so that plants can access them, and are thus important stimulants for plant growth. It has further been found that different kinds of soil formations have different complements of naturally occurring microorganisms that contribute to the fertility of the soil for various crop and natural plant species to take root and flourish. For example, the Desert Institute of the Chinese Academy of Sciences has found in desert soils that, in sand, the primary surface layer microorganisms were found to be Fragilaria, Oscillatoria willei, and Phormidium okenii. Where the surface layer is an algal crust the primary microorganisms were found to be Synechococcus parvus, Tychonema granulatum and Phormidium retzli. Where the surface layer is a lichen crust the primary microorganisms were found to be Oscillatoria wille, Oscillatoria carboniciphila and Phormidium retzli. In the case of the moss crust surface layer, the primary microorganisms were found to be Synechococcus parvus, Synechocystis pavalekii and Phormidium retzli. It is particularly beneficial to nurture such natural colonies to form, particularly in arid regions were reestablishment of natural flora can be beneficial to soil stabilization and to the increased production of natural plant colonies in replenishing the soil with carbon and other nutrients. The Institute has reported that certain species of these microorganisms are prevalent in soil samples in the Gobi and nearby deserts in China, and these species are of particular interest as potential members of the population of organisms to be incorporated into the final biofertilizer formulation of this invention. For example, see the recent report by Yanmei Liu et al on "The Effects of Soil Crusts on Soil Nematode Communities Following Dune Stabilization in the Tennger Desert, Northern China" Applied Soil Ecology, vol 49, pp 118-124 (2011).

Many of the microorganisms in the BSC are also photosynthetic and draw their energy from sunlight such that they can, in-turn, manufacture and provide nutrition and fixed nitrogen to cohort microorganisms that are not photosynthetic or are found deeper in the soil. The actions of the BSC, and the deeper cohort microorganisms to which it supplies nutrition, work together to stabilize soil and draw plant available nutrition from the grains of soil into the soil matrix over time. Importantly, the dominant cyanobacteria component of BSC fixes carbon as well as nitrogen from the atmosphere. Beginning with BSC, the combined actions of these microorganisms create conditions benefiting the establishment and growth of vascular plants like grasses, shrubs and crops. In effect, the BSC is a naturally occurring solar powered fertilizer that lives on the surface of bare earth making it suitable and beneficial for the establishment of vascular plants over time. However, because BSC microorganisms reproduce slowly in dry climates and are not very motile, physical disturbances like tilling, livestock grazing, and fire can halt the BSC's beneficial effects for the soil and the BSC, and these benefits can take decades or centuries in dry climates to naturally restore.

The production of the preferred biofertilizer rapidly reproduces naturally occurring select BSC microorganisms at an industrial scale in a PBR. The microorganisms are then carefully compounded to form "inoculant seeds" of these microorganisms that constitute the preferred biofertilizer, and that are spread onto land presently lacking healthy soil crust colonies, thus accelerating the natural recovery of the soil. As the biofertilizer propagates on the soil surface, it draws down increasing amounts of carbon from atmospheric CO2 into the soil where that carbon becomes part of a living sustainable microbiological community and effectively sequesters this atmospheric carbon into the soil. Through soil inoculation with the preferred biofertilizer, its natural propagation on the soil and secondary vascular plant growth enhancement, it has been estimated that the conversion of 1 ton of CO2 into the preferred biofertilizer, which is then applied onto suitable soils, can cause the drawdown of up to 50 tons of CO2 from the atmosphere annually through direct photosynthetic uptake of atmospheric gasses.

The cyanobacteria and their soil consortia used to produce the biofertilizer are preferably cultured into an inoculum in a manner taught by U.S. Patent Application Publication No. US 2008/0236227 to Flynn, the contents of which are hereby incorporated by reference in their entirety, (herein after referred to as "Flynn") and used to inoculate an amplifying PBR, also taught by Flynn, where the culture can be rapidly grown in liquid media via ready access to nutrients, carbon dioxide, sunlight and hydraulic mixing. The PBR may be fed by sunlight, nutrients and a carbon source that is most commonly carbon dioxide, but that may be a fixed form such as sodium bicarbonate or other bio-available forms.

A preferred method for producing the biofertilizer in accordance with the present invention includes the following steps:

(1) Isolating the important photosynthetic biological soil crust microorganisms to produce a polyspecies culture that closely reflects the native microbial species composition;

(2) Cultivating the culture in a PBR, preferably under controlled conditions designed to maximize biomass productivity;

(3) Harvesting the produced biomass by, for example, a simple gravity-driven sedimentation and filtration, clarification, or centrifugation;

(4) Preferably adding separately produced diazotrophic microorganisms to the biomass;

(5) Preserving the biomass by, e.g., using refractance window drying technology, or other methods such as air drying, spray drying, vacuum drying, or freezing such that the cells remain viable; and (6) Pulverize, flake, or powder the dried cyanobacteria and diazotrophic microorganisms to facilitate packaging, storage, shipment, and final dissemination of the biofertilizer.

After growing in the PBR, the soil microorganisms being harvested, and preferably mixed with diazotrophic microorganisms, are compounded using admixes and coatings to create the product biofertilizer. The biofertilizer can be spread upon farmlands or damaged land using standard agricultural practices, such as crop dusting, mixing with irrigation water or applying with spreading machines. Once on the soil surface, the natural availability of carbon dioxide and nitrogen in air, along with available participation or irrigation water and sunlight, causes the biofertilizer to induct a growing colony of soil microorganisms in proportion with the suitability of growth conditions for that specific consortium of microorganisms.

The consortium of microbes in a locally adapted biofertilizer is preferably drawn from a desired target outcome soil patch that represents the best and most desired microbiological outcome for the treated soil, and that is similar in non-biological constitution and environmental factors to the soil in the area to be treated. In this way, a consortium of microorganisms can be specifically selected to manufacture a particular regional type of biofertilizer that includes microorganisms most favored to survive, thrive and fertilize on the targeted soil to be treated in that region. When this is done and the biofertilizer is spread to sufficient surface density, then the crust will reestablish at an accelerated rate well in advance of natural propagation. In land reclamation efforts, sufficient application density is approximately 0.1 to 2 biofertilizer particles per square cm. In agricultural applications where accelerated fertilization performance is required, sufficient application density is approximately 1 to 20 biofertilizer particles per square cm.

As microorganisms grow and propagate in and on the soil, their uptake of CO2 from the atmosphere increases proportionate with the population size, impinging sunlight, water availability, soil type and the occurrence of secondary vascular plant growth that might further increase the net primary productivity of the soil. The amount of CO2 drawn down from the atmosphere will vary widely dependent on these factors. It is estimated that if a crust is allowed to grow to maturity in a land reclamation application, that it will draw down from the atmosphere approximately 100 grams of CO2 per square meter per year.

The purpose of the inoculation PBR is to obtain the organisms from the target outcome soil and begin growing a population facsimile within the PBR's liquid medium. The population generated by the inoculation PBR should have substantially the same or otherwise sufficient microorganism consortia members and in roughly substantially the same or otherwise sufficient balance as they were present natively in the soil. The PBR operator uses input and output population and growth media assay data to adjust growth input parameters such as light, pH, temperature, CO2 and nutrient levels, as well as mixing speed to effect the desired growth rate and population balance characteristics on the output of the incubator. In a similar fashion, the amplifier and production PBR operator looks at the population and growth media assay between the input and output of the PBRs and adjusts the same growth conditions to affect the desired result. In some cases, the desired product population ratio may be different from that found in the target outcome soil, but will affect a better result upon application via that difference.

The pH and rate of photosynthesis in the PBR system can be measured using the PT4 Monitor, available from Point Four Systems Inc. (Richmond, British Columbia Canada), which includes the controller, acquisition software, dissolved oxygen, pH, and temperature probes. The difference in dissolved oxygen between the lower and upper probe arrays provides a measure of photosynthesis. Likewise, the difference in pH between the lower and upper probe arrays is a measure of CO2 consumption. Under illumination, the microorganisms will photosynthesize and assimilate CO2 causing the pH of the medium to rise. When the pH increases to a chosen set point, preferably pH 7.5, the controller will introduce 100% CO2 into the PBR, which will cause the pH to drop as a result of the formation of carbonic acid and related complexes.

The output of the PBR may be fed into filtering and drying belts in which various optional admixes can be applied. The resultant dry flake and its optional coating may then be granulated to become the biofertilizer. The final biofertilizer product can be distributed and applied to soil via various agricultural and land restoration spreaders. Advantageously, the biofertilizer pellets can be broadcast by a spinning spreader or aircraft such that they are not blown away by the ambient wind. The biofertilizer can also be mixed with irrigation water and sprayed on crops.

The various admixes optionally to be included also desirably remain physically associated with the microorganism consortium in the same relative proportions, even as the composite admix/biomass flake is reduced in size by granulation. By even layering and infusing of the admix homogeneously across the flake as the flake is being generated, then these relative proportions of admix/biomass can be maintained during the granulation and particle coating process. The dry admix components may be further added as the biomass mat begins to consolidate, which helps to mechanically consolidate them with the biomass by entrapping some of the dry admix in the filaments of the consolidating cyanobacteria. The wet admix is typically, but not exclusively, a sugar based composition of xero-protectants and heterotrophic consortium member nutrition additive that serve to bind and glue all the components together as it dries. Using an actual mucilage or other water soluble glue for this purpose, or a solvent based but UV degradable binder, can also be considered for this purpose.

The following are optional admixes and their purpose:

1) Anti-oxidants such as beta carotene can preserve the biofertilizer during the drying process and in storage.

2) Xero-protectants such as sucrose and other sugars, or a biologically derived xero-protectant called trehalose can prevent cell damage from rapid desiccation and extended desiccation over time.

3) Growth nutrients include micro nutrients needed by all soil microorganisms as taught by Flynn including sugars to feed the non-photosynthetic cohorts during the initial stages of establishment.

4) Sand or clay fillers serve two purposes. One is to increase the weight density of the resultant granulated particles thereby making them more aerodynamically spreadable from aircraft and land based spreaders and resistant to wind currents. The other purpose is to provide a non-damaging location for fracture lines between the desiccated microorganisms during granulation that does not split through the microorganism itself 5) Spread pattern tracers may be fluorescent additives. Another tracing tag may be the use of inheritable but non-operational-unique gene sequences within one of the microorganisms that will propagate at the same rate and with the same spatial characteristics as the biofertilizer propagates. This will allow a researcher or carbon credit auditor to visit a patch of soil months or years after initial application of the biofertilizer and know how much of the soil crust or under-earth biomass is directly due to the propagation and beneficial actions of the specifically tagged biofertilizer.

6) Vascular plant seeds like restorative grasses or actual crop seeds may become part of admix. In this case the biofertilizer would be designed to work in biological concert with the embedded vascular plant seeds to achieve and maximize the desired restorative of fertilizing result.

7) A tackifier may be added to the admix in order to quickly bind the particle with other soil grains upon first environmental wetting to prevent further shifting by wind or water erosion.

8) Other microorganisms may be added to either the dry mix or to the wet mix. These other microorganisms may be chosen for their auxiliary properties like being a good tackifier or they may be chosen because they are an important part of the biological consortium of the biofertilizer; yet for various reasons such as growth media type incompatibility or susceptibility to predation they were not able to be co-grown in the same PBR as the rest of the biofertilizer consortium members.

9) Biochar from the pyrolysis of biomass is added to, among other things, enhance the overall carbon content and to provide a strong adsorbent for various other mineral and cyanobacteria components. This will alter the overall water and nutrient retention potential of the formulated biofertilizer and allow it to be tailored to specific crop and geographic locations needs.

10) Inorganic ash from biomass pyrolysis and oxidation of 60 the resulting residue may be added to the formulated biofertilzer to control the overall K delivery potential and to adjust the overall pH of the soil to be treated. Here again, the levels can be adjusted to the needs of specific crops or soil treatment protocols. Other inorganic elements may be added from combustion or pyrolysis related processing, especially those operated in an integrated fashion with the biofertilizer production process of this invention. Materials containing alkali or alkaline earth metals with sulfur or nitrogen containing counterions are particularly useful. Calcium sulfate and nitrate salts, potassium nitrate and other nitrogen bearing salts are also useful.

Biologics may also be spray coated onto the exterior of the particle. In this context "biologics" can refer to whole living or dead cells or bio-active substances that affect the receptivity of the soil to being colonized by the biofertilizer microorganisms. Alternatively, these substances may be intended to prevent the consumption or destruction of the biofertilizer by other living organisms such as insects, other microorganisms, birds or other living creatures.

A preferred method of producing the structured biochar is via microwave pyrolysis with representative results provided below.

| | feed-stock 1 wheat straw | feed-stock 2 corn stover | feed-stock 3 cotton gin | feed-stock 4 |
|---|---|---|---|---|
| proximate analysis | | | | |
| moisture content, | 7.40% | 7.50% | 7.87% | 13.70% |
| ash content, | 5.90% | 4.70% | 6.97% | 7.80% |
| volatile matter, | 69.30% | 70.20% | 69.54% | 68.40% |
| fixed carbon | 17.40% | 17.50% | 15.62% | 10.10% |
| ultimate analysis/ elemental analysis | | | | |
| carbon, C | 41.41% | 43.51% | 45.28% | 49,70% |
| hydrogen, H | 5.86% | 6.23% | 5.14% | 6.98% |
| oxygen, O (by difference) | 45.22% | 43.88% | 47.06% | 24.43% |
| nitrogen, N | 1.44% | 1.52% | 1.58% | 10.92% |
| sulfer, S | 0.17% | 0.16% | 0.40% | 0.17% |

Further investigation of the microwave pyrolysis route shows that individual properties of the biochar can be varied by controlling the overall energy input, catalyst (e.g., K2CO3 or Na2CO3) loading and operating conditions of the system.

Biochar Characterization (Wheat Straw) Effects of Operation Conditions

| | micro-wave power, Watt | Specific area (m2/g, BET) | specific Volume of pores (cm3/g) | averaged pore diameter (A°) |
|---|---|---|---|---|
| 10 wt % Biochar | 600 | 128.71 | 0.094 | 29.23 |
| 10 wt % K2CO3 | 400 | 8.09 | 0.011 | 52.01 |
| 10 wt % K2CO3 | 600 | 6.97 | 0.010 | 58.78 |
| 10 wt % Na2CO3 | 600 | 12.69 | 0.015 | 47.22 |
| 10 wt % K2CO3 | 800 | 8.91 | 0.010 | 46.28 |

Additionally, these phenomena is also observed with other pyrolysis temperatures as shown below.

Biochar Characterization (Wheat Straw) Effects of Pyrolysis Temperatures

| pyrolysis temperature | Specific area (m2/g, BET) | specific Volume of pores (cm3/g) | averaged pore diameter A°) |
|---|---|---|---|
| 400° C. | 0.89 | 0.006 | 282.16 |
| 500° C. | 3.33 | 0.010 | 118.59 |
| 600° C. | 9.81 | 0.012 | 46.64 |

Ultimate Analysis of Biochar (Wheat Straw) Effects of Operation Conditions

| | carbon, C | hydrogen, H | oxygen, O (by difference) | nitro-gen, N | sulfur, S |
|---|---|---|---|---|---|
| 10 wt % Biochar | 46.85 | 0.78 | 45.94 | 0.54 | n.d. |
| 5 wt % Na2CO3 | 59.85 | 1.37 | 31.85 | 1.02 | n.d. |
| 10 wt % Na2CO3 | 61.79 | 1.65 | 29.35 | 1.32 | n.d. |
| 20 wt % Na2CO3 | 64.63 | 1.78 | 26.45 | 1.24 | n.d. |
| 10 wt % K2CO3 | 61.42 | 1.65 | 30.07 | 0.96 | n.d. |
| 20 wt % K2CO3 | 60.85 | 2.07 | 30.24 | 0.95 | n.d. |

Ultimate Analysis of Biochar Effects or Pyrolysis Temperature

| pyrolysis temperature | carbon, C | hydrogen, H | oxygen, O (by difference) | nitrogen, N | sulfur, S |
|---|---|---|---|---|---|
| 400° C. | 52.18 | 2.79 | 37.30 | 1.06 | 0.77 |
| 500° C. | 53.01 | 2.49 | 36.26 | 0.94 | 1.40 |
| 600° C. | 53.67 | 2.34 | 35.49 | 0.92 | 1.68 |

As can be seen from the above, it is possible to tailor the overall active surface area of the biochar component by controlling the operating conditions in the pyrolysis step—and thereby controlling the overall porosity and absorptivity of the biochar component in the formulated biofertilizer. The preferred range of average pore sizes for biochar used as an algae nucleation site range from 20 up to 400 angstroms. Biochar for use as an inorganics absorption medium preferably has average pore sizes ranging from 40 up to 200 angstroms. Biochar used as a fertilizer component as a water retention medium preferably has average pore sizes from 20 to 400 angstroms, more preferably from 100-400 angstroms. The concentrations of biochar included in the fertilizer composition range from 10 up to 50% wt of the final formulation.

Similarly, it is possible to vary the overall surface area, the total potassium K level and the available total alkali by controlling the ratio of raw biochar from non-catalyzed pyrolysis combined with biochar from a step where specific levels of $K_2CO_3$ or other alkali or alkaline earth oxides or salts were added to the biomass prior to pyrolysis. Characteristics and illustrative methods of preparation of biochar are described in the thesis of Pavithra Sellaperumal submitted to the McGill University in partial fulfillment of the requirements of the degree of Master of Science in Bioresource Engineering entitled Evaluation Of The Thermochemical Decomposition Of Various Lignocellulosic Biomasses For Biochar Production, August 2011.

In order to minimize the $CO_2$ footprint in the system of the invention and convert substantially all of the $CO_2$ to algae, produced $CO_2$ is preferably stored during periods of low light or darkness when there is not enough light for photosynthesis to drive $CO_2$ consumption by algae biomass production. To further minimize the $CO_2$ footprint on a lifecycle basis in accordance with the invention, the algae is then used as a biofertilizer, preferably in accordance with the above described system. Coupling these steps together allows for recovery and reuse of the equivalent of as much as 270 times the $CO_2$ conversion to algae alone using an open pond or PBR without the use of artificial light. Without storage, the quantity of $CO_2$ reused is reduced by a factor of two or more. Techniques for storage of $CO_2$ include liquefaction of the $CO_2$, conversion of the $CO_2$ to ammonium bisulfide or urea by well-known conventional chemical processes, physical storage and others.

The Novel process integration of the invention also enables the more effective utilization of by-product streams from one section of the IBTL facility as feedstocks for another. This superior design improves overall efficiency and eliminates a critical barrier to entry by reducing overall investment by 15-20%, thereby allowing the generation of nearly twice the value per ton of biomass versus alternative biomass to liquids routes.

There are several commercial systems available for separating hydrogen from carbon monoxide. Pressure swing adsorption (PSA) processes rely on the fact that under pressure, gases tend to be attracted to solid surfaces, or "adsorbed". The higher the pressure, the more gas is adsorbed; when the pressure is reduced, the gas is released, or desorbed. PSA processes can be used to separate gases in a mixture because different gases tend to be attracted to different solid surfaces more or less strongly. Syngas mixtures of H2, CO and $CO_2$ can be separated by PSA to produce streams rich in hydrogen. Alternatively, syngas can be first subjected to water gas shift to produce a binary mixture of H2 and $CO_2$ which can be separated by PSA or by other means known in the art such as membrane separation (where H2 permeates much more effectively than $CO_2$ to generate pure hydrogen streams). Finally active metal membranes of palladium and other related metal alloys may be used to separate hydrogen from other gases and commercially available options have been produced. U.S. Pat. Nos. 5,792,239, 6,332,913 and 6,379,645, and published applications Nos. US2003/3190486 and US2009/0000408 describe various ones of such separation techniques and are hereby incorporated by reference in their entireties.

The $CO_2$ recovery can be conducted using various conventional recovery processes including, but not limited to, adsorption, absorption (e.g. pressure swing adsorption (PSA) and displacement purge cycles (DPC)), cryogenic separation, membrane separation, combinations thereof and the like. While one or more recovery processes may be needed to recover $CO_2$ from syngas or tail gas, by-product gas from a reformer or C3+ product upgrades will not contain appreciable amounts of $H_2$ or $H_2O$ and thus may not need any recovery process except for condensation of heavy hydrocarbons (C6+). Additionally, while it is desirable to use recovered $CO_2$ in processes of the present invention, it is also possible to supplement or replace recovered $CO_2$ with $CO_2$ obtained from alternative sources within an integrated complex.

Product streams from the process of the present invention can include, for example, a synthetic crude and other individual product streams such as liquefied petroleum gas (C3-C4), condensate (C5-C6), high-octane blend components (C6-C10 aromatic-containing streams), jet fuel, diesel fuel, other distillate fuels, lube blend stocks or lube blend feedstocks that can be produced and sold as separate products.

Illustrative Biofertilizer Production Procedures

Many different strains of bacteria can be used beneficially as components of a biofertilizer. An illustrative method for the production of the diazotrophic organisms, Rhizobium, Azotobacter and Azasprillum, involves the following steps except the broth or liquid medium used is preferably different for different organisms. The preferred mediums used for the respective organisms are:

i) Rhizobium: Yeast Extract Mannitol ii) Azotobacter: Ashby's medium iii) Azospirillium: Medium formulated by Okon et al. (1977)

iv) Phosphate solubilizing bacteria: Pikiyskaya's medium.

1. Preparation of Mother or Starter Cultures:

Starter cultures of selected diazotrophic strains are obtained after ascertaining their performance in green house and at field levels. The pure cultures of efficient strains of nitrogen fixing diazotrophic organism are grown on the respective agar mediums on slant and maintained in the laboratory. A loop full of inoculum from each slant is transferred to respective 250 ml capacity conical flasks containing the appropriate liquid mediums. The conical flasks are kept on a rotary shaker for between 3 and 7 days depending whether the organisms are fast or slow growing. The content of the flasks, called mother or starter cultures, usually attains a load of $10^5$-$10^6$ cells per ml. This mother cultures are further multiplied in larger flasks.

2. Preparation of Broth Cultures:

An equal quantity the appropriate liquid mediums for the respective organisms are prepared in large conical flasks (1000 ml) and sterilized in an autoclave for ½ hour at 15 lbs pressure. After sterilization, each flask is inoculated with the mother culture in 1:5 proportions aseptically. The flasks are kept on a rotary shaker for 96-120 hours until the viable count per ml reaches to $10^9$ cells. The broths become more thick in consistency. This broth culture should not be stored at ambient temperature for more than 24 hours, or, if stored for a longer period, should be maintained at a temperature of 4° C.

3. Preparation of Carrier:

The carrier should have following characters:::

a) A high organic matter—above 60%.

b) Low soluble salts—less than 1%.

c) High moisture holding capacity—150 to 200% by weight.

d) Provide a nutritive medium for growth of bacteria and prolong their survival in culture as well as on inoculated seed.

Structured biochar is a preferred carrier, and lignite or peat may also be used as a carrier, in the preparation of biofertilizers. The carriers are crushed and powdered to 200 to 300 mesh. Peat or Lignite powder should be neutralized by addition of 1% calcium carbonate (CaCO3) and sterilized at 15 lbs pressure for 3-4 hours in autoclave.

4. Preparation of Inoculate:

The sterilized and neutralized lignite, peat or other carrier material is mixed with high count broth culture in galvanized trays. About 1 part by weight of broth is required to 2 part of dry carrier. Final moisture content varies from 40 to 50% depending upon the quality of the carriers.

5. Curing or Maturation:

After mixing the broth cultures and carrier powder in the galvanized trays, the trays are kept for curing at room temp (~28° C.) for 5 to 10 days. After curing, the contents of the trays are sieved to disperse concentrated pockets of growth and to break up lumps.

6. Filling and Packing:

After curing, the sieved powders are stored in polythene bags of 0.5 mm thickness, leaving ~⅔ of the space in the bags open for aeration of the bacteria and bags are sealed.

7. Storage:

The inoculants should be stored in a cool place away from direct heat, preferably at a temp of 15° C. and not exceeding 30° C.+/−2° C. for a maximum of six months. For longer survival of the microorganisms, the bags should be in cold storage at a temperature of 4° C.

Culturing of Microorganisms

The preferred media led the mass production of Rhizobium, Azospirillum, Azotobacter and Phosphobacteria are as follows:

Rhizobium: Yeast Extract Mannitol Broth.

Growth on Congo Red Yeast Extract Mannitol Agar Medium

| | |
|---|---|
| Mannitol | 10.0-12.0 g |
| K2 HPO4 | 0.5-0.8 g |
| Mg SO4—7H2 O | 0.2-0.5 g |
| NaCl | 0.1-0.3 g |
| Yeast extract | 0.5-0.8 g |
| Agar | 20.0-20.0 g |
| Distilled water | 1000.0 ml |

Add 10 ml of Congo red stock solution (250 mg of Congo red dissolved in 100 ml water) to 1 liter water after adjusting the PH to 6.8 and before adding agar.

Azospirillum: Dobereiner's Malic Acid Broth with NH4Cl (1 g Per Liter)

Composition of the N-Free Semisolid Malic Acid Medium

| | |
|---|---|
| Malic acid | 5.0-10.0 g |
| Potassium hydroxide | 4.0-8.0 g |
| Dipotassium hydrogen orthophosphate | 0.5-0.8 g |
| Magnesium sulphate | 0.2-0.4 g |
| Sodium chloride | 0.1-0.2 g |
| Calcium chloride | 0.2-04 g |
| Fe-EDTA (1.64% w/v aqueous) | 4.0-6.0 ml |
| Trace element solution | 2.0-4.0 ml |
| BTB (0.5% alcoholic solution) | 2.0-4.0 ml |
| Agar | 1.75-2.75 g |
| Distilled water | 1000 ml |
| PH | 6.8-6.9 |
| Trace element solution | |
| Sodium molybdate | 200-250 mg |
| Manganous sulphate | 235-255 mg |
| Boric acid | 280-290 mg |
| Copper sulphate | 8-10 mg |
| Zinc sulphate | 24-40 mg |
| Distilled water | |

Azotobacter: Waksman Medium No. 77 (N-Free Mannitol Agar Medium)

| | |
|---|---|
| Mannitol | 10.0-15.0 g |
| Ca CO3 | 5.0-8.0 g |
| K2HPO4 | 0.5-0.8 g |
| Mg SO4•7H2O | 0.2-0.4 g |
| NaCl | 0.2-0.4 g |
| Ferric chloride | Trace |
| MnSO4•4H2O | Trace |
| N-free washed Agar | 15.0-20.0 g |
| pH | 7.0 |
| Distilled Water | 1000 ml |

Phosphobacteria: Pikovskaya's Broth

| | |
|---|---|
| Glucose | 10.0-15.0 g |
| Ca(PO4)2 | 5.0-8.0 g |
| (NH4)2SO4 | 0.5-0.8 g |
| KCl | 0.2-0.4 g |
| MgSO4•7H2O | 0.1-0.2 g |
| MnSO4 | Trace |
| FeSO4 | Trace |
| Yeast Extract | 0.5-0.8 g |
| Distilled Water | 1000 ml |

The broth is prepared in flasks and inoculum from mother culture is transferred to flasks. The culture is grown under shaking conditions at 30±2° C. as submerged culture. The culture is incubated until maximum cell population of $10^{10}$ to $10^{11}$ cfu/ml is produced. Under optimum conditions this population level could be attained within 4 to 5 days for Rhizobium; 5 to 7 days for Azospirillum; 2 to 3 days for Phosphobacteria and 6-7 days for Azotobacter. The culture obtained in the flask is called starter culture. For large scale production of inoculant, inoculum from starter culture is transferred to large flasks/seed tank fermenter and grown until required level of cell count is reached.

Bacterial growth in batch culture can be modeled with four different phases: lag phase (A), log phase or exponential phase (B), stationary phase (C), and death phase (D).

1. During lag phase, bacteria adapt themselves to growth conditions. It is the period where the individual bacteria are maturing and not yet able to divide. During the lag phase of the bacterial growth cycle, synthesis of RNA, enzymes and other molecules occurs.
2. The log phase (sometimes called the logarithmic phase or the exponential phase) is a period characterized by cell doubling. The number of new bacteria appearing per unit time is proportional to the present population. Under controlled conditions, cyanobacteria can double their population four times a day. Exponential growth cannot continue indefinitely, however, because the medium is soon depleted of nutrients and enriched with wastes.
3. The stationary phase is often due to a growth-limiting factor such as the depletion of an essential nutrient, and/or the formation of an inhibitory product such as an organic acid. Stationary phase results from a situation in which growth rate and death rate are equal.
4. At death phase, (Decline phase) bacteria run out of nutrients and die.

Inoculum Preparation

The following is an illustrative procedure for the preparation of an algae or diazotrophic organism inoculum.

- Inoculate 500 ml, 3 liter and 5 liter flasks containing the appropriate media with the corresponding starter or mother culture (at log phase).
- Large quantities of the above media are prepared in a fermenter, sterilized and cooled.
- The media in the fermenter is inoculated with the log phase culture grown in 5 liter flask. Usually 1-2% inoculum is sufficient, however inoculation is done up to 5% depending on the growth of the culture in the larger flasks.
- The cells are grown in the fermenter by providing aeration (passing sterile air through compressor and sterilizing agents like glass wool, cotton wool, acid etc.) and given continuous stirring.
- The broth is checked for the population of inoculated organism and contamination if any at the growth period.
- The cells are harvested with the population load of $10^9$ cells/ml after the incubation period.
- There should not be any fungal or any other bacterial contamination at $10^{-6}$ dilution level
- It is not advisable to store the broth after fermentation for periods longer than 24 hours. Even, at 4° C. the number of viable cells begins to decrease.

Processing of Carrier Material

The use of appropriate carrier material contributes to the production of good quality biofertilizer. Peat soil, lignite and biochar are preferred carrier materials. Vermiculite, charcoal, press mud, farmyard manure and soil mixture can also be used as a carrier. Neutralized peat soil and lignite have the advantages of being relatively low cost, high in organic matter content, non-toxic, easy to process and have a water holding capacity of more than 50%.

The carrier material is made it into a powder so as to pass through 212 micron IS sieve.

The pH of a peat soil and lignite carrier material is neutralized with calcium carbonate (1:10 ratio), since the are acidic (pH of 4-5)

The neutralized carrier material is sterilized in an autoclave to eliminate any contaminants.

Preparation of Inoculants Packet

The neutralized, sterilized carrier material is spread in a clean, dry, sterile metallic or plastic tray.

The bacterial culture drawn from the fermenter is added to the sterilized carrier and mixed well. The culture suspension is added to a level of 40-50% water holding capacity depending upon the population. This concentration corresponds to an incipient wetness point where the powder can hold half again as much moisture and still be free flowing.

The inoculant is packed in polythene bags in 200 g quantities, which are sealed and allowed to cure for 2-3 days at room temperature.

The polythene bags should be of low density grade and have a thickness of about 50-75 micron.

Mass Production and Use of Mycorrhizal Diazotrophic BioFertilizer

The following is an illustrative method for the production of mycorrhizal (AM) fungi:

A trench (1 m×1 m×0.3 m) is formed and lined with black polythene sheet to be used as a plant growth tub.

Mixed 50 kg of vermiculite and 5 kg of sterilized soil and packed in the trench up to a height of 20 cm.

Spread 1 kg of AM inoculum (mother culture) 2-5 cm below the surface of vermiculite.

Maize seeds surface sterilized with 5% sodium hypochlorite for 2 minutes are sown.

Applied 2 g urea, 2 g super phosphate and 1 g muriate of potash for each trench at the time of sowing seeds. Further 10 g of urea is applied twice on 30 and 45 days after sowing for each trench.

Quality test on AM colonization in root samples is carried out on 30th and 45th day.

Stock plants are grown for 60 days (8 weeks). The inoculum is obtained by cutting all the roots of stock plants. The inoculum produced consists of a mixture of vermiculite, spores, pieces of hyphae and infected root pieces.

Within 60 days 55 kg of AM inoculum could be produced from the 1 sq meter area. This inoculum is sufficient to treat 550 $m^2$ nursery area having 11,000 seedlings.

For nursery application, the use of 100 g bulk Vermiculite Supported AM (VAM) fungi inoculum per square meter is sufficient. The inoculum should be applied at 2-3 cm below the soil surface at the time of sowing. The seeds/cutting should be sown/planted above the VAM inoculum to cause infection.

For polythene bag raised crops: 5 to 10 g bulk VAM inoculum is sufficient for each packet. Mix 10 kg of inoculum with 1000 kg of sand potting mixture and pack the potting mixture in polythene bag before sowing.

For out-planting: Twenty grams of VAM inoculum is required per seedling. Apply inoculum at the time of planting.

For existing trees: Two hundred gram of VAM inoculum is required for inoculating one tree. Apply inoculum near the root surface at the time of fertilizer application.

Mass Production and Field Application of Cyanobacteria

Blue green algal (BGA) inoculation with composite cultures has been found to be more effective than single culture inoculation. A technology for mass scale production of composite culture of blue green algae under rice field condition was developed and it was found that the soil based BGA inoculum could survive for more than 2 years. At many sites where algal inoculation was used for three to four consecutive cropping seasons, the inoculated algae establish well and the effect persisted over subsequent rice crops.

The blue green algal inoculum may be produced by several methods viz., in tubs, galvanized trays, small pits and also in field conditions closed or open PPR's. However large-scale production under field condition, which is easily adopted by farmers is frequently preferable.

I. Multiplication in Trays

Large metallic trays (6'×3'×6"lbh) can be used for small scale production

Take 10 kg of paddy field soil, dry the powdered soil well and spread

Fill water to a height of 3"

Add 250 g of dried algal flakes (soil based) as inoculum

Add 150 g of super phosphate and 30 g of lime and mix well with the soil

Sprinkle 25 g carbofuran to control the insects

Maintain water level in trays

After 10 to 15 days, the blooms of BGA will start floating on the water sources

At this stage stop watering and drain. Let the soil to dry completely

Collect the dry soil based inoculum as flakes

Store in a dry place. By this method 5 to 7 kg of soil based inoculum can be obtained.

II. Multiplication Under Field Conditions

Materials

Rice field

Super phosphate

Carbofuran

Composite BGA starter culture

Procedure

Select an area of 40 m2 (20 m×2 m) near a water source which is directly exposed to sunlight. Make a support wall all around the plot to a height of 15 cm and coat it with non permeable layer of plastic or dense sand to prevent loss of water due to percolation.

Plot is well prepared and levelled uniformly and water is allowed to a depth of 5-7.5 cm and left to settle for 12 hrs.

Apply 2 kg of super phosphate and 200 g lime to the plot uniformly over the area.

The soil based composite starter culture of BGA containing 8-10 species @ 5 kg is powdered well and broadcast.

Carbofuran @ 200 g is also applied to control soil insects occurring in BGA.

Water is let in at periodic intervals so that the height of water level is always maintained at 5 cm.

After 15 days of inoculation, the plots are allowed to dry up in the sun and the algal flakes are collected and stored. Alternatively, dissolved air floatation or other separation means may be used to isolate the BGA cells from water.

The floating algal flasks are green or blue green in color. From each harvest, 30 to 40 kg of dry algal flakes are obtained from the plot.

III Method of Inoculation of BGA in a Rice Field

Blue green algae may be applied as soil based inoculum to the rice field following the method described below.

Powder the soil based algal flakes.

Mix it with 10 kg soil or sand (10 kg powdered algal flakes with 10 kg soil/sand).

BGA is to be inoculated on 7-10 days after rice transplanting.

Water level at 3-4" is to be maintained at the time of BGA inoculation and then for a month so as to have maximum BGA development.

A week after BGA inoculation, algal growth can be seen and algal mat will float on the water after 2-3 weeks. The algal mat color will be green or brown or yellowish green.

While the individual microorganisms may be applied separately to the field, it is normally preferable to apply multi-component mixtures of these organisms in a single application using a physical mixture of cyanobacteria, diazotrophic organisms and structured biochar. In this manner, we eliminate the need for serial application of the individual components.

Mass Production and Field Application of Azolla Diazotrophic Organisms

Azolla is a free-floating water fern that floats in water and fixes atmospheric nitrogen in association with nitrogen fixing blue green alga Anabaena azollae. Azolla fronds consist of sporophyte with a floating rhizome and small overlapping bi-lobed leaves and roots. Azolla is used as biofertilizer for wetland rice and it is known to contribute 40-60 kg N ha-1 per rice crop. In accordance with the invention, Azolla is applied in combination with structured biochar and blue green algae either in a single application or serially as a biofertilizer having substantially improved characteristics over Azolla alone.

I. Mass Multiplication of Azolla Under Field Conditions

A simple Azolla nursery method for large scale multiplication of Azolla in the field has been developed for easy adoption by farmers.

Materials

One cent (40 sq.m) area plot

Cattle dung

Super phosphate

Furadan

Fresh Azolla inoculum

Procedure

Select a wetland field and prepare thoroughly and level uniformly.

Mark the field into one cent plots (20×2 m) by providing suitable bunds and irrigation channels.

Maintain water level to a height of 10 cm.

Mix 10 kg of cattle dung in 20 liters of water and sprinkle in the field.

Apply 100 g super phosphate as basal dose.

Inoculate fresh Azolla biomass @ 8 kg to each pot.

Apply super phosphate @ 100 g as top dressing fertilizer on 4th and 8th day after Azolla inoculation.

Apply carbofuran (furadan) granules @ 100 g/plot on 7th day after Azolla inoculation.

Maintain the water level at 10 cm height throughout the growth period of two or three weeks.

Harvest the Azolla mat floating on the plot, drain the water and record the biomass.

II. Method of Inoculation of Azolla to Rice Crop

The Azolla BioFertilizer may be applied in different ways for the wetland paddy. In a first method, fresh Azolla biomass is inoculated in the paddy field before transplanting and incorporated as green manure. This method requires huge quantity of fresh Azolla. In the other method, Azolla may be inoculated after transplanting rice and grown as dual culture with rice and incorporated subsequently.

A. Azolla Biomass Incorporation as Green Manure for Rice Crop

Collect the fresh Azolla biomass from the Azolla nursery plot.

Prepare the wetland well and maintain water just enough for easy incorporation.

Apply fresh Azolla biomass (15 t ha-1) to the main field and incorporate the Azolla by using implements or tractor.

B. Azolla Inoculation as Dual Crop for Rice

Select a transplanted rice field.

Collect fresh Azolla inoculum from Azolla nursery.

Broadcast the fresh Azolla in the transplanted rice field on 7th day after planting (500 kg/ha).

Maintain water level at 5-7.5 cm.

Note the growth of Azolla mat four weeks after transplanting and incorporate the Azolla biomass by using implements or tractor or during inter-cultivation practices.

A second bloom of Azolla will develop 8 weeks after transplanting which may be incorporated again.

By the two incorporations, 20-25 tons of Azolla can be incorporated in one hectare rice field. The Azolla may also be first dried and pulverized and processed in a manner similar that described above for the other diazotrophic organisms. In all cases the Azolla is combined with structured biochar and blue green algae in the biofertilizer.

Application of Biofertilizer

The biofertilizer of the invention may be applied either as seed treatment or seed inoculation, as a seedling root dip, or by main field application For seed treatment, one packet of the inoculant is mixed with 200 ml of rice kanji to make a slurry. The seeds required for an acre are mixed in the slurry so as to have a uniform coating of the inoculant over the seeds and then shade dried for 30 minutes. The shade dried seeds should be sown within 24 hours. One packet of the inoculant (200 g) is sufficient to treat 10 kg of seeds.

The seedling root dip, method is used for transplanted crops. Two packets of the inoculant is mixed in 40 liters of water. The root portion of the seedlings required for an acre is dipped in the mixture for 5 to 10 minutes and then transplanted.

In main field application, four packets of the inoculant are mixed with 20 kgs of dried and powdered farm yard manure and then broadcasted in one acre of main field just before transplanting.

Rhizobium

For all legumes Rhizobium is applied as seed inoculant.

Azospirillum/Azotobacter

In the transplanted crops, Azospirillum is inoculated through seed, seedling root dip and soil application methods. For direct sown crops, Azospirillum is applied through seed treatment and soil application.

Phosphobacteria

Inoculated through seed, seedling root dip and soil application methods as in the case of Azospirillum. Combined application of bacterial BioFertilizers.

Phosphobacteria can be mixed with Azospirillum and Rhizobium. The inoculants should be mixed in equal quantities and applied as mentioned above.

Guidelines

Bacterial inoculants should not be mixed with insecticide, fungicide, herbicide and chemical fertilizers.

Seed treatment with bacterial inoculant is to be done at last when seeds are treated with fungicides.

BioFertilizers Recommendation (One Packet—200 g)

| S. No. | Crop | Seed | Nursery | Seedling dip | Main field | Total Dosage Requirement of Packets per ha |
|---|---|---|---|---|---|---|
| 1. | Rice | 5 | 10 | 5 | 10 | 30 |
| 2. | Sorghum | 3 | — | — | 10 | 13 |
| 3. | Pearl millet | 3 | — | — | 10 | 13 |
| 4. | Ragi | 3 | — | 5 | 10 | 18 |
| 5. | Maize | 3 | — | — | 10 | 13 |
| 6. | Cotton | 3 | — | — | 10 | 13 |
| 7. | Sunflower | 3 | — | — | 19 | 13 |
| 8. | Castor | 3 | — | — | 10 | 13 |
| 9. | Sugarcane | 10 | | | 36 (3 split) | 46 |
| 10. | Turmeric | — | — | — | 24 (2 split) | 24 |
| 11. | Tobacco | 1 | 3 | — | 10 g/pit | 14 |
| 12. | Papaya | 2 | — | — | 10 | — |
| 13. | Mandarin Orange | 2 | — | — | 10 g/pit | — |
| 14. | Tomato | 1 | — | — | 10 | 14 |
| 15. | Banana | — | — | 5 | 10 g/pit | — |

Rhizobium (Only Seed Application is Recommended)

| S. No. | Crop | Total Dosage Requirement of Packets per ha |
|---|---|---|
| 1. | Soybean | 5 |
| 2. | Groundnut | 5 |
| . | Bengalgram | 5 |
| 4. | Blackgram | 3 |
| 5. | Green ram | 3 |
| 6. | Redgram | 3 |
| 7. | Cowpea | 3 |

Phosphobacteria The recommended dosage of Azospirillum is adopted for phosphobacteria inoculation; for combined inoculation, both BioFertilizers as per recommendations are to be mixed uniformly before using.

What is claimed is:

1. A method for converting biomass to liquid fuels and/or chemical feedstocks and cyanobacteria based biofertilizer, comprising the steps of:

a. liquefying a biomass feed by hydroprocessing said feed under conditions and for a time sufficient for producing hydrocarbon liquids;

b. upgrading hydrocarbon liquids produced by step a to produce liquid fuels and/or chemical feedstocks;

c. producing structured biochar and byproduct $CO_2$ by microwave pyrolysis of biomass residues produced in step a;

d. producing cyanobacteria in a photobioreactor (PBR) with the use of byproduct $CO_2$ produced by one or both of said direct liquefaction and biochar producing steps; and e. producing a biofertilizer incorporating structured biochar and cyanobacteria produced in steps c and d.

2. The method of claim 1 including controlling the conditions of said pyrolysis such that said structured biochar has an average pore size in the range of 20 to 400 Angstroms.

3. The method of claim 1 further including adding diazotrophic microorganisms for inclusion in said biofertilizer.

4. The method of claim 2 further including removing inorganics from the biomass feed prior to said liquefaction or from said hydrocarbon liquids by absorbing said inorganics in structured biochar having an average pore size in the range of 40 to 200 angstroms.

5. The method of claim 4 further including incorporating structured biochar having an average pore size in the range of 40 to 200 angstroms and containing absorbed inorganics in said biofertilizer.

6. The method of claim 5 wherein said absorbed inorganics include phosphorus, potassium or other metals.

7. The method of claim 4 further including using structured biochar having an average pore size in the range of 20 to 200 angstroms in the PBR as nucleation sites for the cyanobacteria production.

8. The method of claim 1 wherein step b also produces byproduct ammonia, and further including using at least part of said byproduct ammonia as a feed in step d.

9. The method of claim 1 wherein the structured biochar incorporated in said biofertilizer includes structured biochar having an average pore size in the range of 100 to 400 angstroms for use as a moisture retention agent.

10. The method of claim 1 wherein the concentration of said structured biochar in said biofertilizer is from 10 up to 50% wt.

11. The method of claim 1 wherein said hydroprocessing conditions include subjecting said biomass to elevated temperatures and pressures in the presence of a solvent and a molybdenum containing catalyst.

12. A method for producing a cyanobacteria based biofertilizer, comprising the steps of:

a. producing structured biochar having an average pore size in the range of 20 to 400 Angstroms by microwave pyrolysis of biomass;

b. supplying $CO_2$ to a photobioreactor (PBR) for producing cyanobacteria; and c. producing a biofertilizer incorporating biochar and cyanobacteria produced in steps a and b, respectively.

13. The method of claim 12 further including adding diazotrophic microorganisms for inclusion in said biofertilizer.

14. The method of claim 12 further including adding structured biochar containing absorbed nutrients to said biofertilizer.

15. A method for enhancing the growth of soybean crops with the use of a biofertilizer, comprising the steps of:

a. liquefying a biomass feed by hydroprocessing said feed under conditions and for a time sufficient for producing hydrocarbon liquids;

b. upgrading hydrocarbon liquids produced by step a to produce liquid fuels, and/or lube blend stocks, and/or chemical feedstocks;

c. producing structured biochar having an average pore size in the range of 20 to 400 Angstroms by microwave pyrolysis of biomass residues produced in step a;

d. producing a biofertilizer incorporating Rhizobium bacteria and structured biochar produced in step c;

e. applying biofertilizer produced in step d to soybean seeds; and f. planting soybean seeds treated in step e.

*16. The method of claim 12 wherein said PBR contains a portion of said structured biochar during the production of said cyanobacteria.*

*17. The method of claim 16 further including adding diazotrophic microorganisms to said cyanobacteria for inclusion in said biofertilizer.*

*18. The method of claim 16 wherein said PBR contains an aqueous phase and wherein the structured biochar in the PBR absorbs nutrients from the aqueous phase.*

*19. The method of claim 18 wherein structured biochar incorporated in said biofertilizer contains said absorbed nutrients.*

* * * * *